US011776679B2

United States Patent
Korani et al.

(10) Patent No.: US 11,776,679 B2
(45) Date of Patent: Oct. 3, 2023

(54) METHODS FOR RISK MAP PREDICTION IN AI-BASED MRI RECONSTRUCTION

(71) Applicant: The Board of Trustees of the Leland Stanford Junior University, Stanford, CA (US)

(72) Inventors: Morteza Mardani Korani, Santa Clara, CA (US); David Donoho, Stanford, CA (US); John M. Pauly, Stanford, CA (US); Shreyas S. Vasanawala, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 342 days.

(21) Appl. No.: 17/196,838

(22) Filed: Mar. 9, 2021

(65) Prior Publication Data
US 2021/0287780 A1 Sep. 16, 2021

Related U.S. Application Data

(60) Provisional application No. 62/987,597, filed on Mar. 10, 2020.

(51) Int. Cl.
*G16H 30/40* (2018.01)
*G16H 30/20* (2018.01)
(Continued)

(52) U.S. Cl.
CPC ............ *G16H 30/40* (2018.01); *G06N 3/08* (2013.01); *G06T 7/0012* (2013.01);
(Continued)

(58) Field of Classification Search
CPC ........ G16H 30/20; G16H 30/40; G06N 3/044; G06N 3/045; G06N 3/047; G06N 3/048;
(Continued)

(56) References Cited

U.S. PATENT DOCUMENTS 10,373,055 B1 * 8/2019 Matthey-de-l'Endroit .................. G06N 7/01
11,468,265 B2 * 10/2022 Chhabra ............. G06F 18/2148
(Continued)

OTHER PUBLICATIONS

Edupuganti et al., "VAE-GAN for Probabilistic Compressive Image Recovery: Uncertainty Analysis", arXiv:1901.11228v1, Jan. 31, 2019, pp. 1-10 (Year: 2019).*
(Continued)

*Primary Examiner* — Nay A Maung
*Assistant Examiner* — Jose M Torres
(74) *Attorney, Agent, or Firm* — Lumen Patent Firm

(57) ABSTRACT

A method is disclosed for generating pixel risk maps for diagnostic image reconstruction. The method produces uncertainty/variance maps by feeding into a trained encoder a short-scan image acquired from a medical imaging scan to generate latent code statistics including the mean $\mu_y$ and variance $\sigma_y$; selecting random samples based on the latent code statistics, $z \sim N(\mu_y, \sigma_y^2)$; feeding the random samples into a trained decoder to generate a pool of reconstructed images; and calculating, for each pixel of the pool of reconstructed images, the pixel mean and variance statistics across the pool of reconstructed images. The risk of each pixel may be calculated using the Stein's Unbiased Risk Estimator on the input density compensated data, that involves calculating the end-to-end divergence of the deep neural network.

2 Claims, 13 Drawing Sheets

(51) Int. Cl.
*G06N 3/08* (2023.01)
*G06T 7/00* (2017.01)
*G06T 11/00* (2006.01)

(52) U.S. Cl.
CPC ........... *G06T 11/003* (2013.01); *G16H 30/20* (2018.01); *G06T 2207/10088* (2013.01)

(58) Field of Classification Search
CPC . G06N 3/08; G06N 3/088; G06N 7/01; G06T 7/0012; G06T 11/003; G06T 2207/10088
See application file for complete search history.

(56) References Cited

U.S. PATENT DOCUMENTS

| 2016/0098820 | A1* | 4/2016 | Rousselle | G06T 5/002 |
| | | | | 345/426 |
| 2018/0114096 | A1* | 4/2018 | Sen | G06V 10/774 |
| 2019/0095798 | A1* | 3/2019 | Baker | G06N 3/084 |
| 2019/0325620 | A1* | 10/2019 | Adler | G06T 7/10 |
| 2020/0388058 | A1* | 12/2020 | Zhang | A61B 6/5294 |
| 2022/0101122 | A1* | 3/2022 | Vahdat | G06N 3/045 |

OTHER PUBLICATIONS

Edupuganti, et al. Uncertainty Quantification in Deep MRI Reconstruction. IEEE Transactions on Medical Imaging, 1-1.2020.

\* cited by examiner

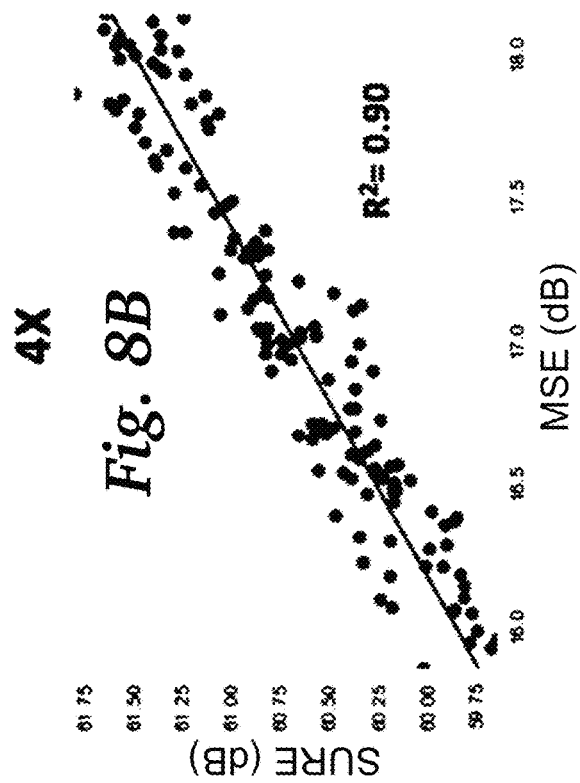
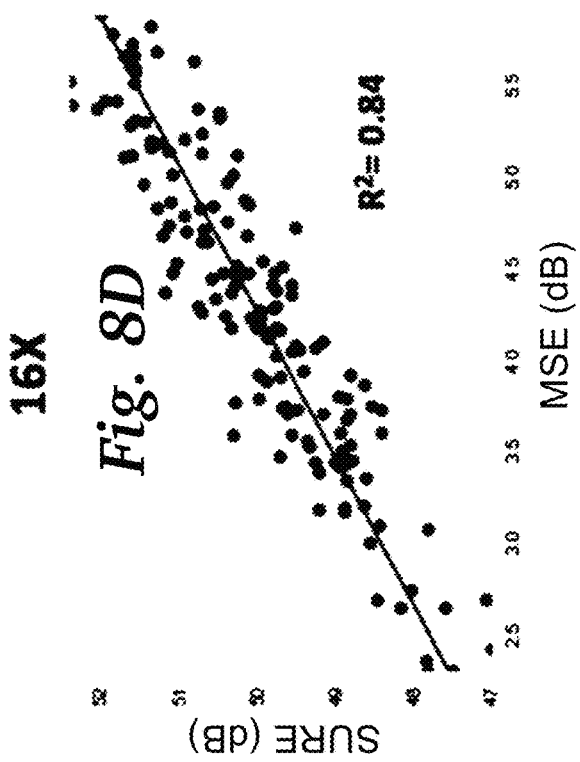
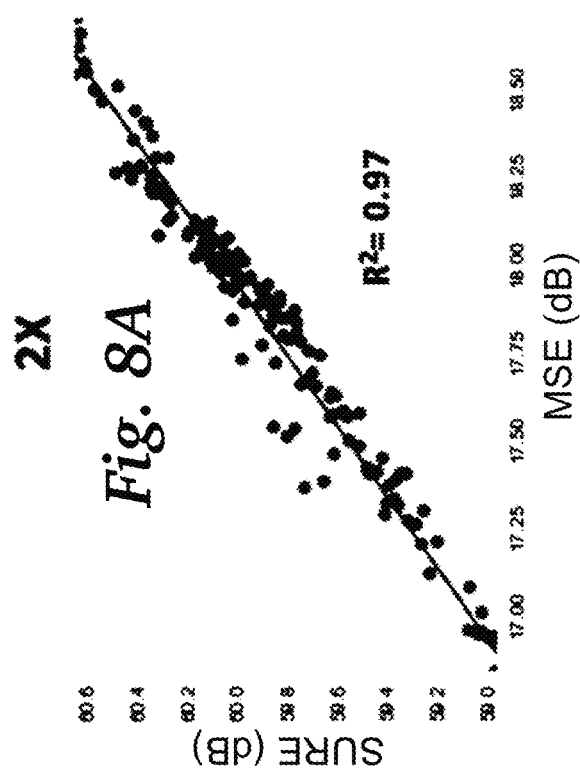
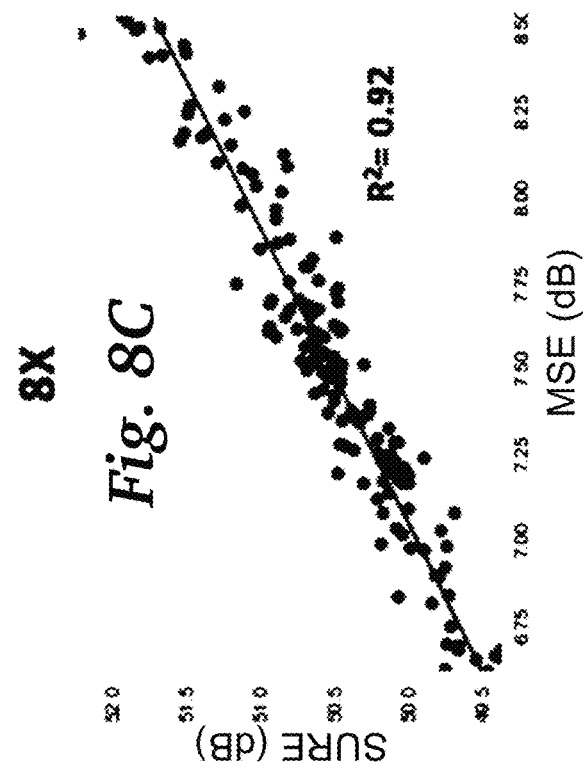

METHODS FOR RISK MAP PREDICTION IN AI-BASED MRI RECONSTRUCTION

CROSS-REFERENCE TO RELATED APPLICATIONS

This application claims priority from U.S. Provisional Patent Application 62/987,597 filed Mar. 10, 2020, which is incorporated herein by reference.

FIELD OF THE INVENTION

The present invention relates generally to methods for image reconstruction in medical diagnostic imaging. More specifically, it relates to methods for assessment of the uncertainty and risk of reconstructed images in AI-based image reconstruction.

BACKGROUND OF THE INVENTION

Reliable MRI is crucial for accurate interpretation in therapeutic and diagnostic tasks. However, undersampling during MRI acquisition as well as the overparameterized and non-transparent nature of deep learning (DL) leaves substantial uncertainty about the accuracy of DL reconstruction.

Artificial intelligence (AI) has introduced a paradigm shift in medical image reconstruction in the last few years, offering significant improvements in speed and image quality [1], [2], [3], [4], [5], [6]. However, the prevailing methods for image reconstruction leverage historical patient data to train deep neural networks, and then use these models on new unseen patient data. This practice raises concerns about generalization, given that predictions can be biased towards the previously-seen training data, and consequently may struggle to detect novel pathological details in the test subjects. This is deeply problematic for both patients and physicians and can potentially alter diagnoses. It is thus crucial to ensure that reconstructions are accurate for new and unseen subjects. This well motivates developing effective and automated risk assessment tools for monitoring image reconstruction algorithms as a part of the imaging pipeline.

Despite the importance of assessing risk in medical image reconstruction, little work has explored the robustness of deep learning (DL) architectures in inverse problems. Not only is the introduction of image artifacts fairly common using such models, but there do not currently exist suitable and generalized empirical methods that enable the quantification of model uncertainty [7]. While other forms of uncertainty, such as those pertaining to the training data and acquisition model, are also important to consider, model uncertainty is especially critical to understand because it explains the unique challenges that DL models can face relative to more traditional techniques for MRI reconstruction.

Medical image reconstruction methods rooted in deep learning have been widely explored. Of the various model architectures that have been used, adversarial approaches based on generative adversarial networks (GANs) are notable for high reconstruction image quality and the ability to realistically model image details. The generator function for these types of architectures is usually a U-net or ResNet [7], [10].

Variational autoencoders (VAEs) have achieved high performance in generating natural images, while also providing probabilistic interpretability of the generation process [11], [12]. However, this approach has not yet been demonstrated in the realm of medical images.

Meanwhile, a small but growing body of work has examined uncertainty in general computer vision problems. Specifically, measurements of uncertainty have been computed by finding the mean and point-wise standard deviation of test images using Monte Carlo sampling with probabilistic models [13]. With such a method, comparing the mean intensities of regions containing an artifact and the surrounding area over several cases can provide statistical insights into the types of errors made by the model [14]. Approximate Bayesian inference based approaches have also been introduced as a way of quantifying model uncertainty [15]. The downside of these methods is that they are only applicable to probabilistic models and not deterministic ones.

Other studies have explored using invertible neural networks to learn the complete posterior of system parameters [16], [17]. Through bootstrapping, point estimate uncertainty can be obtained statistically and analyzed in a manner similar to posterior sampling. Models such as convolutional neural networks (CNNs) have also been applied on MRI reconstructions to obtain global uncertainty scores, though these models can introduce their own uncertainty and may themselves suffer from challenges with robustness [18].

Uncertainty has also been analyzed from the standpoint of data rather than variance introduced by generative models in the context of medical imaging [19]. Techniques such as the bootstrap and jackknife can be used on the sampled input data to produce accurate error maps that provide insight into the most risky ROIs in terms of reconstructions without having access to the ground truth.

Stein's Unbiased Risk Estimator (SURE) has also seen some use in imaging applications. Specifically, SURE has been utilized in regularization and for image denoising, where it is explicitly minimized during the optimization step [20], [21]. However, it has not been widely used in uncertainty estimation or in the context of medical imaging.

Given that most existing approaches of quantifying uncertainty do not apply broadly or are constrained by the chosen models, developing straightforward and effective techniques is very important. Such methods have the potential to enable holistic comparison and evaluation of model architectures across a range of problems, leading to increased robustness in sensitive domains.

BRIEF SUMMARY OF THE INVENTION

The invention provides method for generating pixel risk maps for generic deep image reconstruction algorithms. The risk maps can be generated in real time, and are universal across various medical imaging modalities. These reconstruction risk maps can be paired along with or overlaid on the reconstructed medical images to guide physicians' analysis and interpretation. The technique calculates a quantitative generalization risk that each pixel is different from the ground-truth pixel, without having access to the ground-truth image which is usually impossible or impractical to obtain.

The techniques of the present invention may be used to quantify the uncertainty in image recovery with DL models. To this end, we first leverage variational autoencoders (VAEs) to develop a probabilistic reconstruction scheme that maps out (low-quality) short scans with aliasing artifacts to the diagnostic-quality ones. The VAE encodes the acquisition uncertainty in a latent code and naturally offers a posterior of the image from which one can generate pixel variance maps using Monte-Carlo sampling. Accurately predicting risk requires knowledge of the bias as well, for which we leverage Stein's Unbiased Risk Estimator (SURE) as a proxy for mean-squared-error (MSE). A range of empirical experiments is performed for Knee MRI reconstruction under different training losses (adversarial and pixel-wise) and unrolled recurrent network architectures. Our key observations indicate that: 1) adversarial losses introduce more uncertainty; and 2) recurrent unrolled nets reduce the prediction uncertainty and risk.

In one aspect, the invention provides a method for generating pixel risk maps for diagnostic image reconstruction comprising: feeding into a trained encoder a short-scan image acquired from a medical imaging scan to generate latent code statistics including the mean $\mu_y$ and variance $\sigma_y$; selecting random samples based on the latent code statistics, $z \sim N(\mu_y, \sigma_y^2)$; feeding the random samples into a trained decoder to generate a pool of reconstructed images; calculating, for each pixel of the pool of reconstructed images, the pixel mean and variance statistics across the pool of reconstructed images.

The method may further comprise calculating quantitative scores for risk of each pixel. This may be performed by computing an end-to-end Jacobian of a reconstruction network that is fed with a density-compensated short-scan image, and estimating the risk of each pixel based on the Stein Unbiased Risk Estimator (SURE).

BRIEF DESCRIPTION OF THE SEVERAL VIEWS OF THE DRAWINGS

FIGS. 8A, 8B, 8C, 8D. SURE vs. MSE for one recurrent block using no adversarial loss, with 2-fold, 4-fold, 8-fold, and 16-fold undersampling, respectively.

DETAILED DESCRIPTION OF THE INVENTION

Figure 1:
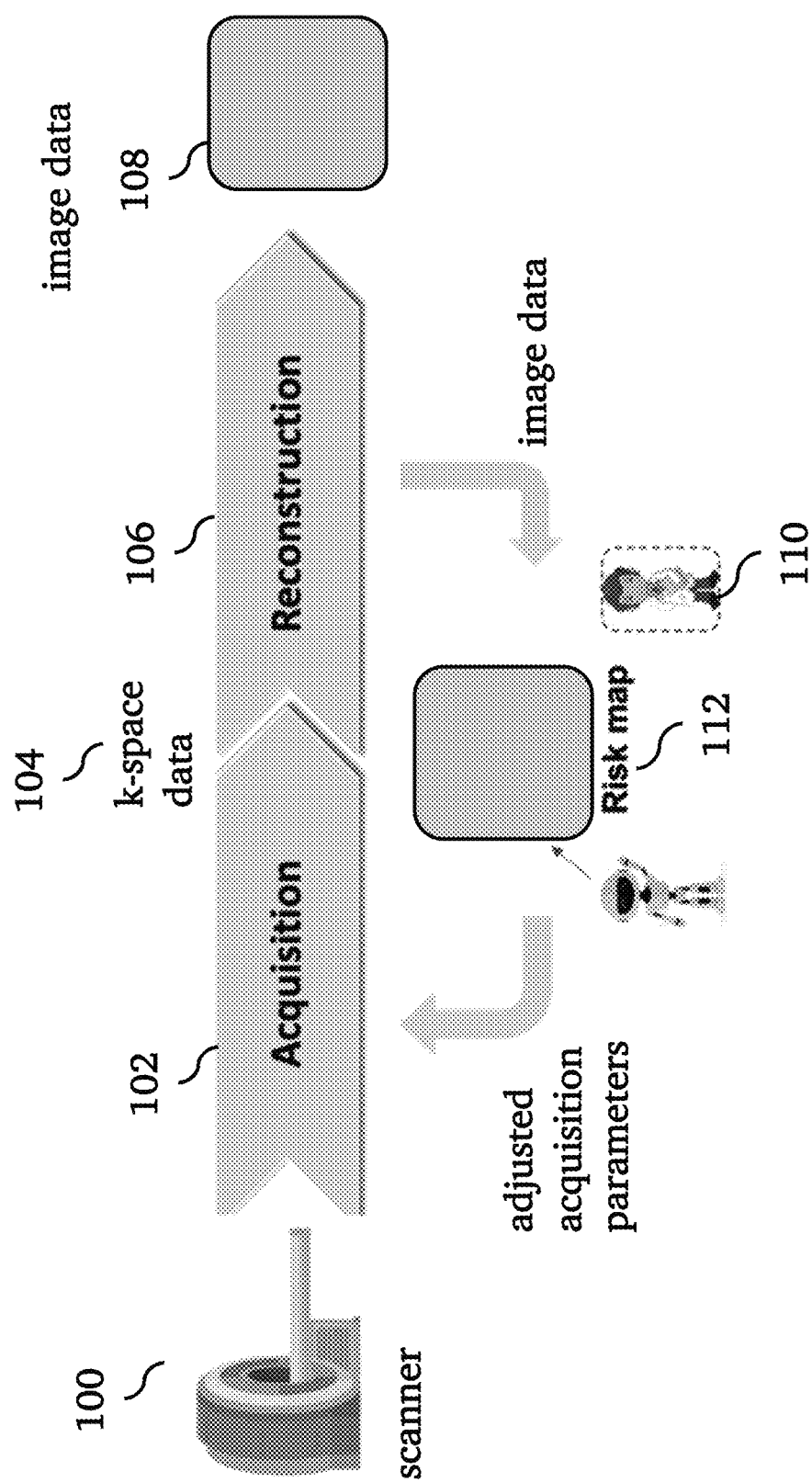
FIG. 1. Processing pipeline for clinical operation. The scanner acquires k-space data, followed by image reconstruction that is subject to artifacts. Traditionally, physicians are in the loop to assess the image quality which is labor intensive and error prone.

Given the pernicious effects that the presence of image artifacts can have, reliable uncertainty quantification methods could have utility both as an evaluation metric and as a way of gaining interpretability regarding risk factors for a given model and dataset [8]. In principle, a radiologist could consider a combination of uncertainty heat maps and the scan being analyzed to make better informed interpretations overall. Additionally, uncertainty information could be leveraged in real time to inform the optimal measurements to acquire during scanning, or alternatively, separate models could be applied in a targeted fashion to enhance quality in specific regions of the image. For example, FIG. 1 illustrates a processing pipeline for clinical operation of diagnostic medical imaging. A medical imaging scanner 100 performs an acquisition 102 to acquire k-space data 104, followed by image reconstruction 106 to produce an image 108 that typically contains artifacts. Traditionally, physicians 110 assess the image quality, which is labor intensive and error prone, and can use that to adjust imaging parameters in the next acquisition. The present invention provides a risk map 112 associated with the reconstructed image 108 to assist the physician or even to enable automated adjustment of acquisition parameters.

To help realize these possibilities, this work introduces procedures that can provide insights into the model robustness of DL MR reconstruction schemes. In doing so, we develop a variational autoencoder (VAE) model for MR image recovery, which is notable for its low error and probabilistic nature which is well-suited to an exploration of model uncertainty. We first generate admissible reconstructions under an array of different model conditions. We then utilize Monte-Carlo sampling methods to better understand the variations and errors in the output image distribution under various model settings [9]. Finally, because accurately assessing bias and error with the Monte Carlo approach requires access to the true (fully-sampled) image, we leverage the Stein's Unbiased Risk Estimator (SURE) analysis of the DL model, which serves as a surrogate for mean squared error (MSE) even when the ground truth is unknown.

Empirical evaluations of these techniques are performed on real-world medical MR image data, considering the single coil acquisition model. Our key observations include: 1) using an adversarial loss function introduces more pixel uncertainty than a standard pixel-wise loss, while better recovering the high-frequencies; 2) a cascaded network architecture better leverages the physical constraint of the problem and results in higher confidence reconstructions 3) SURE effectively approximates MSE and serves as a valuable tool for assessing risk when the ground truth reconstruction (i.e. fully sampled image) is unavailable.

Important contributions of this work are as follows:
A novel VAE scheme for learning inverse maps that produces pixel uncertainty maps
Quantifying risk using SURE by taking into account the end-to-end network Jacobian
Evaluations and statistical analysis of uncertainty for various network architectures and training losses.

Preliminaries and Problem Statement

One key application of inverse problems is to Magnetic Resonance Imaging (MRI), where significant undersampling is typically employed to accelerate acquisition, leading to challenging image recovery problems. As a result, the development of accurate and rapid MRI reconstruction methods could enable powerful applications like diagnostic-guided surgery or cost-effective pediatric scanning without anesthesia [22], [23].

In MR imaging, the goal is to recover the true image $x_0 \in \mathbb{C}^n$ from undersampled k-space measurements $y \in \mathbb{C}^m$ with m n that admit $$y = \Phi x_0 + v. \qquad (1)$$

Here, $\Phi$ in general includes the acquisition model with the sampling mask $\Omega$, the Fourier operator F, as well as coil sensitivities (in the multi-coil setting). The noise term v also accounts for measurement noise and unmodeled dynamics.

Figure 2:
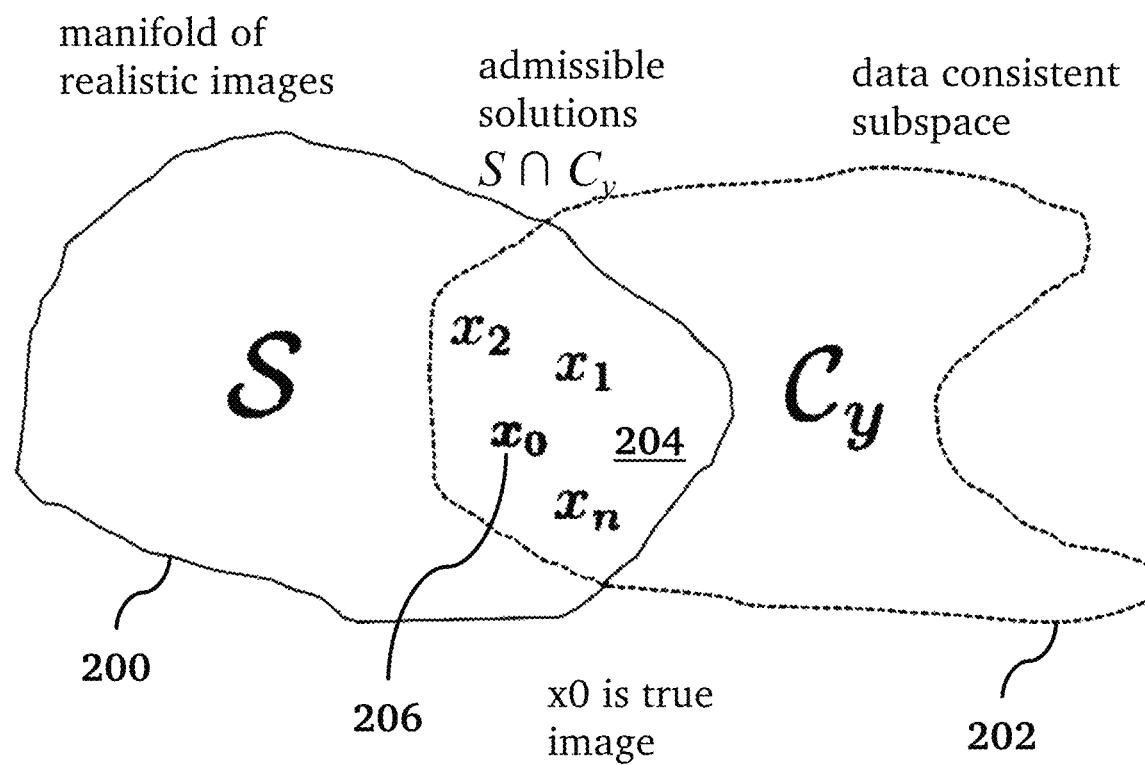
FIG. 2. Admissible solutions ($x_0$ is the true image).

Given the ill-posed nature of this problem, it is necessary to incorporate prior information to obtain high-quality reconstructions. This prior information spans across a manifold of realistic images 200 ($S \subset \mathbb{C}^n$) as shown in FIG. 2. However, since not all points on this manifold are consistent with the measurements, we must consider the intersection 204 of the prior manifold 200 S with a data consistent subspace 202 $C_y := \{x \in \mathbb{C}^n : y = \Phi x + v\}$. Note that the intersection 204 $S \cap C_y$ contains the true solution 206 $x_0$, and also might contain multiple other admissible solutions $x_1, \ldots, x_n$ with different likelihoods.

While DL models can be effectively used for learning the projection onto the intersection 204 $S \cap C_y$, performance can be limited when seeing new data unlike the training examples. In particular, one risk is the introduction of realistic artifacts, or so-termed "hallucinations," which can prove costly in a domain as sensitive as medical imaging by misleading radiologists and resulting in incorrect diagnoses [24], [25]. Hence, analyzing the uncertainty and robustness of DL techniques in MR imaging is essential.

To address this challenge, the techniques of the present invention are able to learn a projection onto the intersection 204 $S \cap C_y$ between the real image manifold S and the data consistent subspace $C_y$ using a DL model, and then evaluate the uncertainty of the model in producing these reconstructions.

Vaes for Medical Image Recovery

For image recovery, we consider a VAE architecture (h), consisting of an encoder f and a decoder g with latent space z. While VAEs have been used successfully in low-level computer vision tasks like super-resolution, they have not been applied to medical image recovery. Importantly, the VAE is capable of learning a probability distribution of realistic images that facilitates the exploration process of the manifold S. By randomly sampling latent code vectors corresponding to specific images and enforcing data consistency, we can traverse the space comprising $S \cap C_y$ and evaluate the results visually and statistically.

Figure 3:
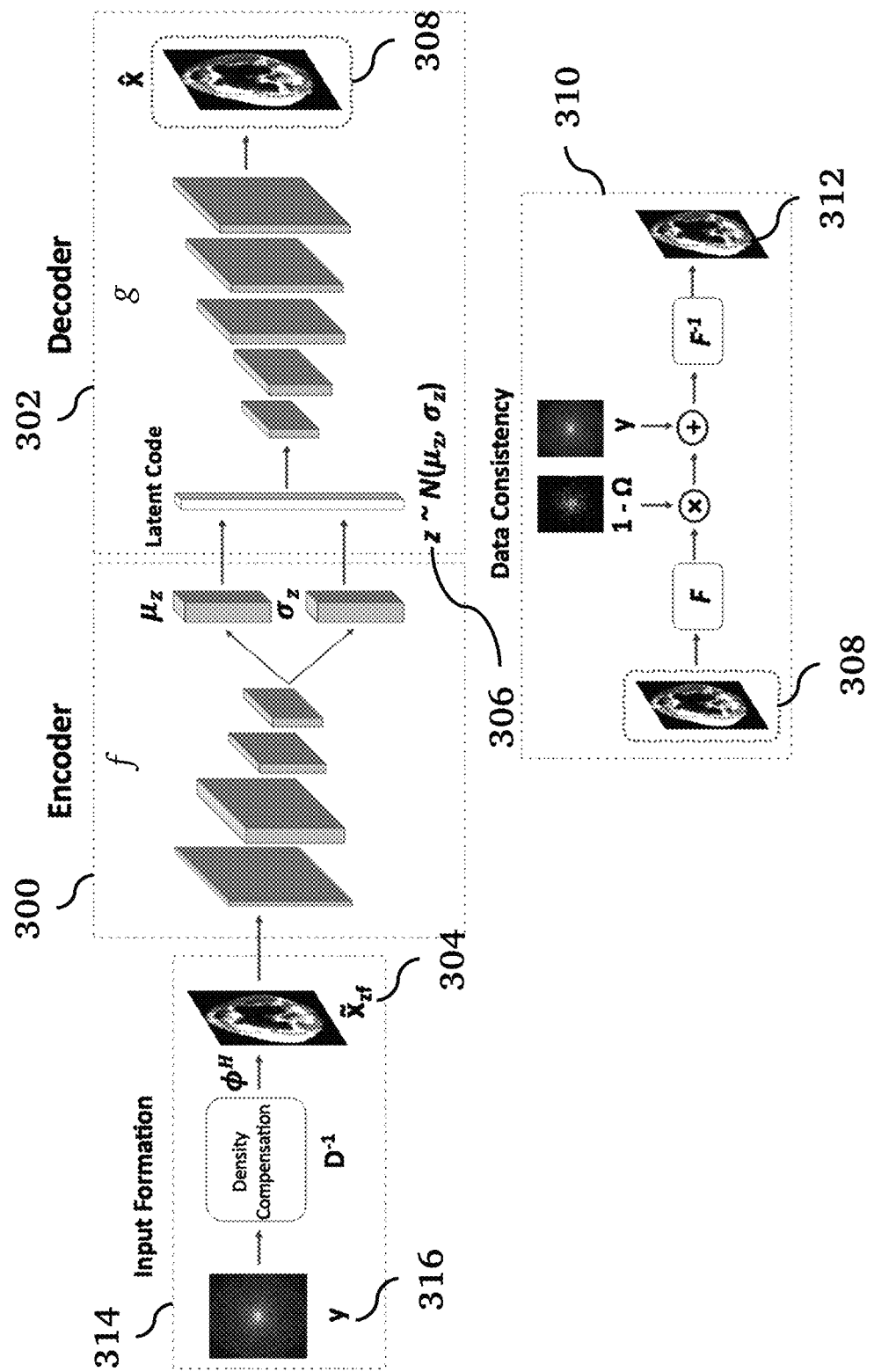
FIG. 3. The model architecture, with aliased input images feeding into the VAE encoder, the latent code feeding into the VAE decoder, and data consistency applied to obtain the output reconstruction. This output can serve as an input to the GAN discriminator (not pictured), which in turn sends feedback to the generator (VAE) when adversarial loss is used. The VAE and data consistency layers are repeated in the case of multiple recurrent blocks.

A processing pipeline is shown in FIG. 3. In an image formation stage 314, undersampled k-space data 316 y obtained from an acquisition by the scanner is used to produce aliased input images 304. These short-scan images 304 are fed as input into the VAE encoder 300 f, which is comprised of convolutional layers that successively compress the short-scan image representation to produce the latent code 306 z, which is a dense layer. The decoder 302 g takes in z as input and in turn uses transpose convolutions for upsampling to produce the reconstructed output image 308. The final reconstruction 312 is obtained by passing this output 308 to the data consistency layer 310, which replaces any known frequencies corresponding to the input (i.e. the measurements collected during acquisition). This output 312 can serve as an input to the GAN discriminator (not pictured), which in turn sends feedback to the generator (VAE) when adversarial loss is used. The VAE and data consistency layers are repeated in the case of multiple recurrent blocks.

More specifically, the VAE functions in the following manner. First, the encoder 300 takes in input $x_{zf}$ 304, which is a poor linear estimate of the true image. Here, $x_{zf} = \Phi^H y$, which is the zero-filled Fourier inverse for the single coil scenario, which we focus on here. For the multi-coil scenario, $x_{zf}$ becomes the SENSE reconstruction taking into account coil sensitivities [26]. The encoder output is q(z|x) (an estimate of the posterior image distribution), where z 306 is an internal latent variable with low dimension. This latent variable formulation is valuable because it enables an expressive family of distributions and is also tractable from the perspective of computing maximum likelihood. Reconstruction occurs through sampling z from q(z|x) and passing the result to the decoder 302. To facilitate sampling, the posterior is represented by a Gaussian distribution and constrained by a prior distribution p(z), which for simplicity of computation is chosen to be the unit normal distribution.

In generating reconstructions, the VAE balances error with the ability to effectively draw latent code samples from the posterior. As such, the VAE loss function used in training is comprised of a mixture of pixel-wise $l_2$ loss and a KL-divergence term, which measures the similarity of two distributions using the expression $$KL(p\|q) = \int p(x) \log[p(x)/q(x)] dx. \qquad (2)$$

where the integral is from $-\infty$ to $+\infty$. In the VAE loss function, the KL term (which has weight $\eta$) is designed to force the posterior (based on $\mu_z$, $\sigma_z$ a for a given batch) to follow the unit normal distribution of our prior p(z) [27], [28]. As $\eta$ increases, the integrity of the latent code (and thereby ease of sampling after training) is preserved at the expense of reconstruction quality.

With reconstruction output $\hat{x} = h(x_{zf})$, the training cost used in updating the weights of the model h is formed as $$\min_h E_{x,y}[\|\hat{x} - x_0\|^2_2] + \eta KL(N(\mu_z, \sigma_z)\|N(0,1)). \qquad (3)$$

At test time, latent code vectors are sampled from a normal distribution $z \sim N(0,1)$ to generate new reconstructions. To ensure that these reconstructions do not deviate from physical measurement, data consistency (obtained by applying an affine projection based on the undersampling mask) is applied to all network outputs, which we find essential to obtaining high signal-to-noise ratio (SNR) [7]. To deepen our analysis of robustness, we also examine the effects of a revised model architecture that is cascaded (i.e. the VAE and data consistency portions of the model repeat) for a certain number of "recurrent blocks," as this can positively impact reconstruction quality [29]. In the case of a model with two recurrent blocks, for example, the zero-filled image is passed into the first VAE, the output of the first VAE is passed as the input of a second VAE, and the output of the second VAE serves as the overall model reconstruction. Data consistency is applied to each VAE in question, and the VAEs have shared weights which ensures that new model parameters are not introduced. Note that we define a model with one recurrent block as the baseline model that has no repetition.

Uncertainty Analysis

The advantage of using a VAE model for image reconstruction is that it naturally offers the posterior of the image which can be used to draw samples and generate variance maps. While these variance maps are useful in letting radiologists understand which pixels differ the most between the model's reconstructions, they are not sufficient since the bias (difference between reconstructions and the fully-sampled ground truth image) is unknown. Thus, methods like SURE which can assess risk without explicitly using the ground-truth are a better alternative. The following subsections introduce these ideas in more detail.

A. Monte Carlo Sampling

An effective way of analyzing the uncertainty of probabilistic models in computer vision problems is to statistically analyze output images for a given input [8]. Nonetheless, this approach has not been widely employed in inverse problems or medical image recovery.

Utilizing the probabilistic nature of the VAE model, for a given zero-filled image $x_{zf} = \Phi^H y$ (i.e. the aliased input to the model), we can use our encoder function $f$ to find the mean $\mu$ and variance $\sigma$ of the latent code z, which we use to draw samples. We can then use our decoder function g to produce reconstructions of latent code samples z and then aggregate the results over k samples to produce pixel-wise mean and variance maps for the reconstructions. Algorithm 1 shows the full sequence of steps in more detail.

This Monte Carlo sampling approach allows one to evaluate variance as well as higher order statistics, which can be very useful in understanding the extent and impact of model uncertainty. However, despite the information the Monte Carlo approach can provide, some important statistics such as bias are dependent on knowledge of the ground truth, which motivates the use of metrics like SURE.

Algorithm 1 Monte Carlo uncertainty map
Input y,Ω,k,f,g
Step 1. Form the input $x_{zf} = \Phi^H y$
Step 2. Generate latent code statistics $(\mu,\sigma) = f(x_{zf})$
Step 3. Initialize i=0, $\hat{x}=[0]_{n \times n}$, and map=$[0]_{n \times n}$
Step 4. While i<k {
  i=i+1
  Draw latent code sample: $z_i \sim N(\mu,\sigma^2)$
  Decode: $\hat{x}_i = g(z_i)$
  Collect reconstructions: $\{\hat{x}_i\}$
}
Step 5. Compute pixel-wise mean and variance: $\hat{x} := (1/k)\Sigma_{i=1,k}\hat{x}_i$,
map:=$(1/k)\Sigma_{i=1,k}(\hat{x}_i - \hat{x})^2$
return ($\hat{x}$, map)

B. Denoising SURE

A useful statistical technique for risk assessment when the ground truth is unknown is Stein's Unbiased Risk Estimator (SURE) [30]. Despite being well-established, SURE has not yet been used for uncertainty analysis in imaging or DL problems. Given the ground truth image $x_0$, the zero-filled image can be written as $$x_{zf} = x_0 + r. \quad (4)$$

where r is what we refer to as the residual term. With reconstruction $\hat{x}$ that has dimension n, test MSE can be expanded as $$E[\|\hat{x} - x_0\|^2] = E[\|x_0 - x_{zf} + x_{zf} - \hat{x}\|] \quad (5)$$

$$= -n\sigma^2 + E[\|x_{zf} - \hat{x}\|^2] + 2\text{Cov}(x_{zf},\hat{x}). \quad (6)$$

Since $x_0$ is not present in this equation, we see that SURE serves as a surrogate for MSE even when the ground truth is unknown. A key assumption behind SURE is that the residual process r that relates the zero-filled image to the ground truth is normal, namely $r \sim N(0,\sigma^2 I)$. With this assumption, we can apply Stein's formula which approximates the covariance to obtain an estimate for the risk as $$\text{SURE} = -n\sigma^2 + \|\hat{x} - x_{zf}\|^2 + \sigma^2 tr(\partial\hat{x}/\partial x_{zf}). \quad (7)$$

Note that SURE is unbiased, namely, $$\text{MSE} = E[\text{SURE}]. \quad (8)$$

With the risk expressed in the above form, we can separate the estimate into three terms, with the second term corresponding to residual sum of squares (RSS) and the third one corresponding to degrees of freedom (DOF). This form importantly does not depend on $x_0$, and approximates the DOF with the trace of the end-to-end network Jacobian $J = \partial\hat{x}/\partial x_{zf}$. The Jacobian represents the network sensitivity to small input perturbations and is a measure of interest when analyzing robustness in computer vision tasks [31].

In order to estimate the residual variance, it is reasonable to assume that error in the output reconstruction is not large, and as a result $\sigma^2$ can be estimated (by setting the sum of the first two terms in the SURE expression to zero) as $$\sigma^2 = \|\hat{x} - x_{zf}\|^2/n. \quad (9)$$

Our evaluations validate this assumption when the undersampling rate is not very large. With this assumption, we can rewrite our expression for SURE as follows $$\text{SURE} = \sigma^2 tr(J). \quad (10)$$

DOF approximation. Due to the high dimension of MR images, computing the end-to-end network Jacobian for SURE can be computationally intensive. From a practical standpoint, making this computation efficient allows one to evaluate uncertainty in real time, in parallel with the reconstruction. To this end, we use an approximation for the Jacobian trace [32]. In particular, given n-dimensional noise vector b drawn from N(0,1), our trained model h and a small value $\epsilon$, the Jacobian trace can be written equivalently as follows $$tr\{J\} = \lim_{\epsilon \to 0} E_{b \sim N(0,1)}[b^T(h(x_{zf} + \epsilon b) - h(x_{zf}))\epsilon^{-1}] \quad (11)$$

Because MR images are high dimensional, taking even a single sample from the above results in a reasonable estimate of the expectation, which yields the following approximation (as a rule of thumb we choose c as the maximum pixel value in the zero-filled image divided by $10^3$) [33].

$$tr\{J\} \approx b^T(h(x_{zf} + \epsilon b) - h(x_{zf}))\epsilon^{-1}. \quad (12)$$

In effect, this expression measures sensitivity of the model output to small perturbations in the input. To make the approximation more accurate, we average it over several (~100) random realizations of b.

Pixel-wise SURE. It is also worth noting that SURE offers not only a global assessment of the reconstruction risk, but can also be used to obtain localized risk maps. To do so, we can easily extend the previous discussion for pixel (i,j) admitting $y_{i,j} = x_{i,j} + r_{i,j}$. The SURE risk per pixel then follows (10) where the Jacobian is a scalar $J(i,j) = \partial x_{i,j}/\partial y_{i,j}$. This version of pixel-wise SURE measures the risk of a pixel in the reconstruction, considering only the pixel at the same spatial position in the input. The primary challenge is accurately estimating $\sigma^2_{i,j}$ which we do by taking the RSS map and averaging each element with the values immediately surrounding it.

Remark 1 [SURE for deterministic networks]. Note that the scope of SURE risk assessment is not limited to variational networks. Indeed, SURE can also be applied to deterministic networks as long as the residuals obey the Gaussian assumption and one can find a reasonable estimate of the residual variance.

C. Gaussian Residuals with Density Compensation

Figure 7A:
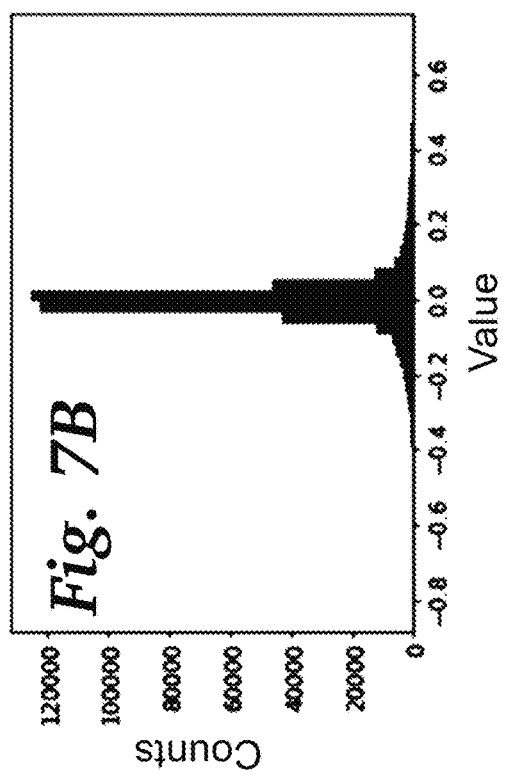
FIGS. 7A-P. Histograms and quantile-quantile plots of the residuals between zero-filled and ground truth images without (FIGS. 7A-H) and with (FIGS. 7I-P) density compensation with 2, 4, 8, and 16-fold undersampling shown in each case.
Figure 7B:
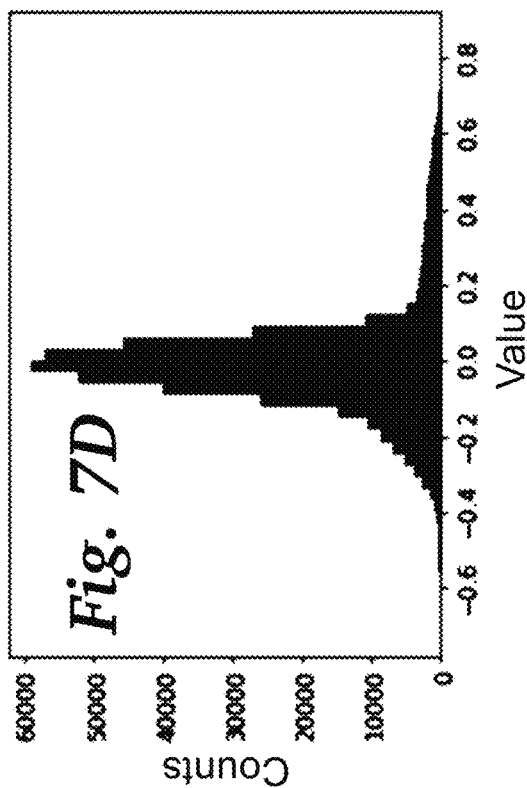
Figure 7C:
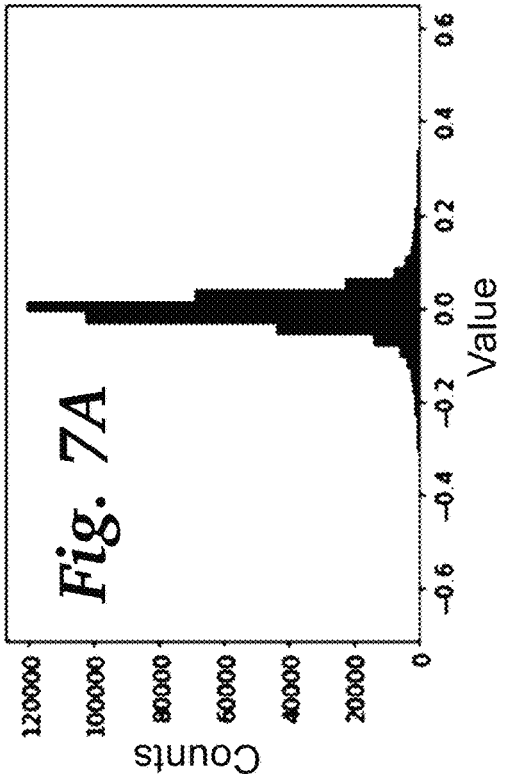
Figure 7D:
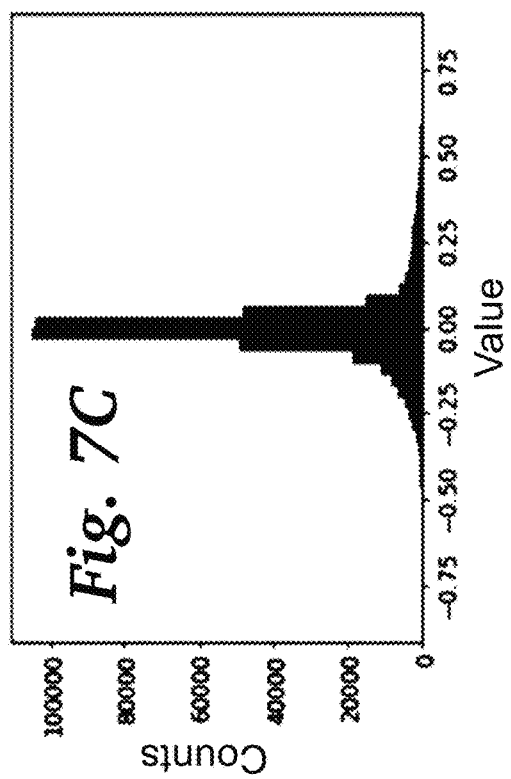
Figure 7F:
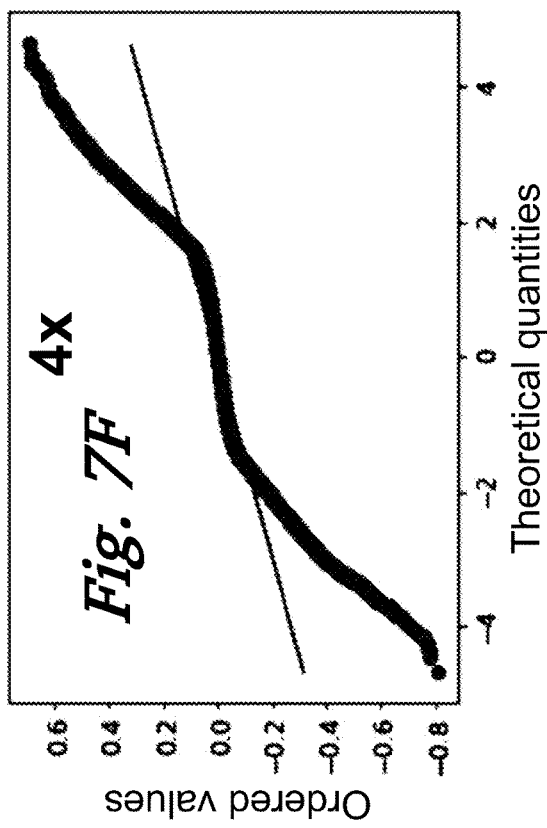
Figure 7H:
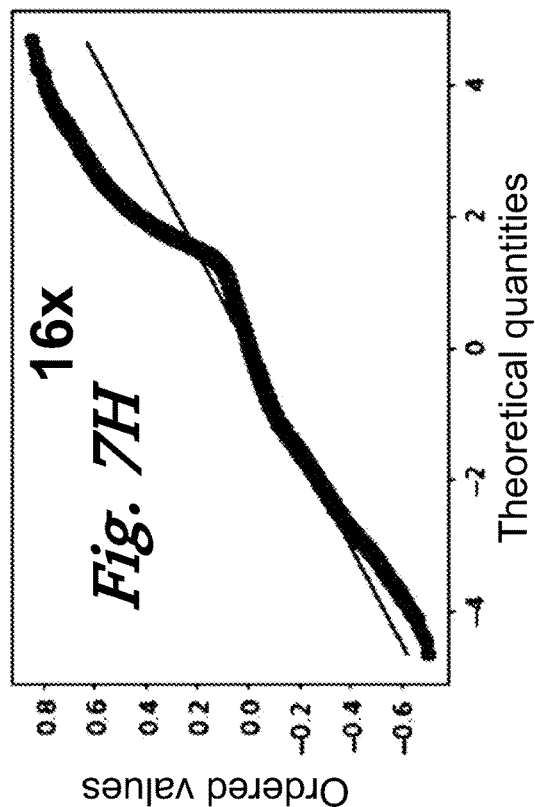
Figure 7E:
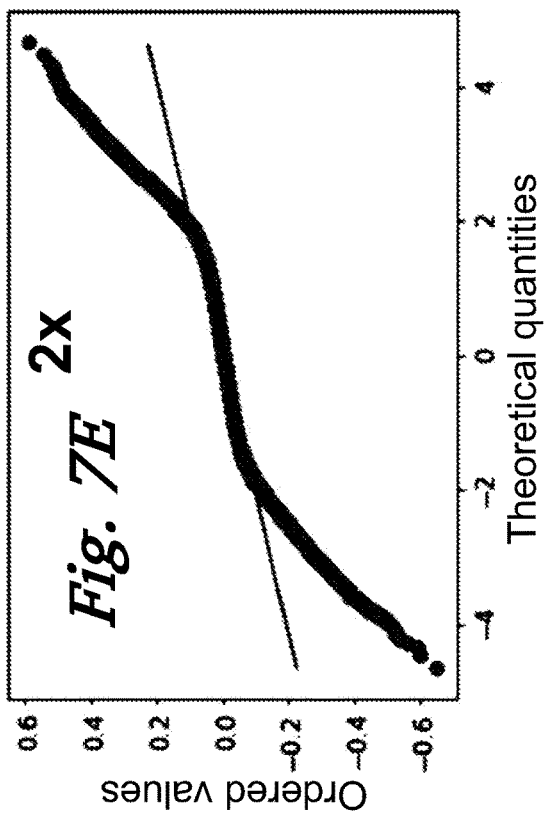
Figure 7G:
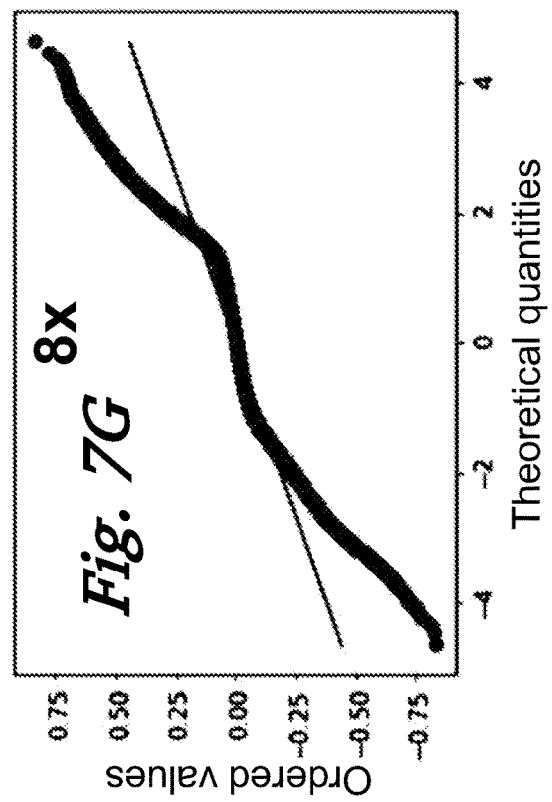
Figure 7J:
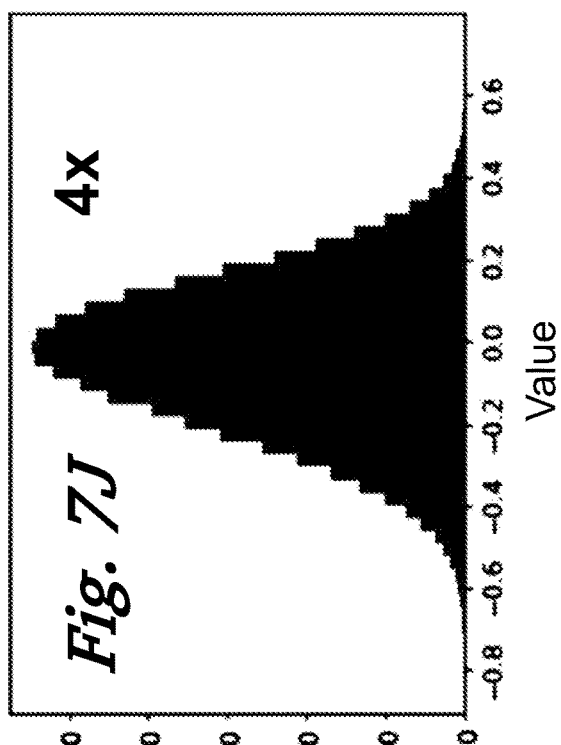
Figure 7L:
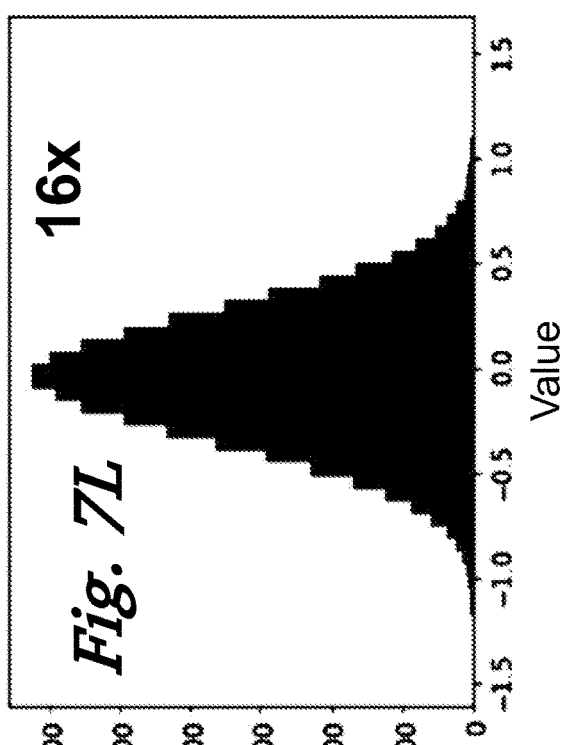
Figure 7I:
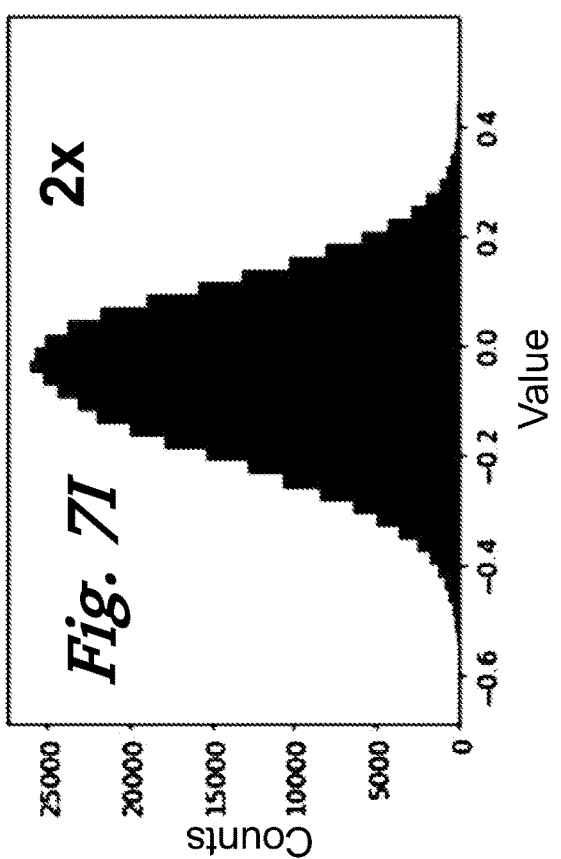
Figure 7K:
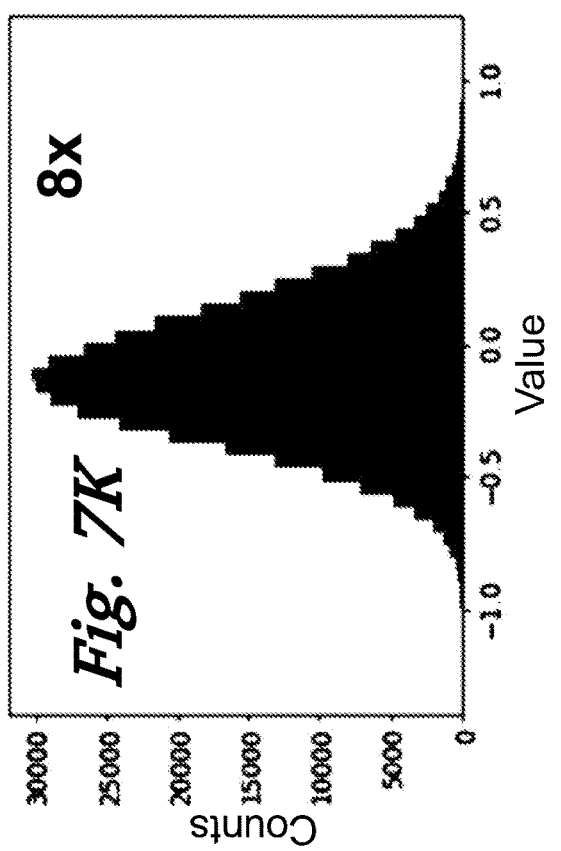
Figure 7M:
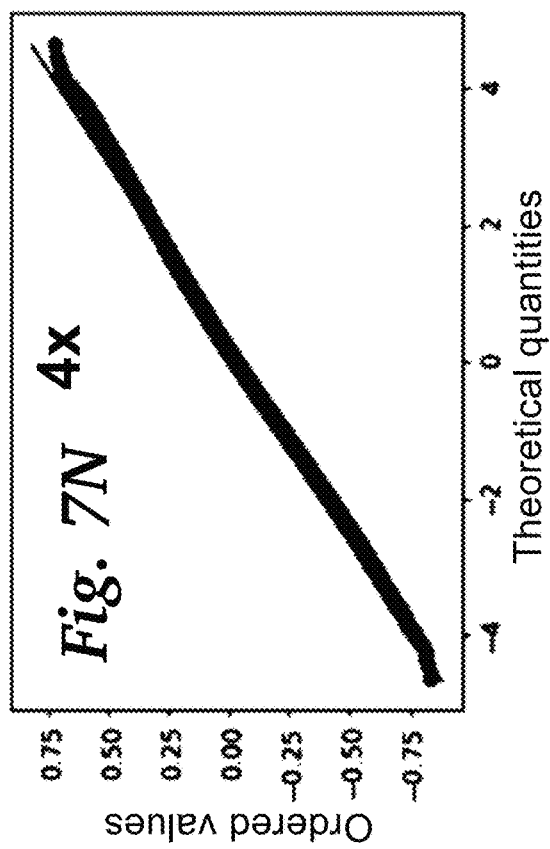
Figure 7N:
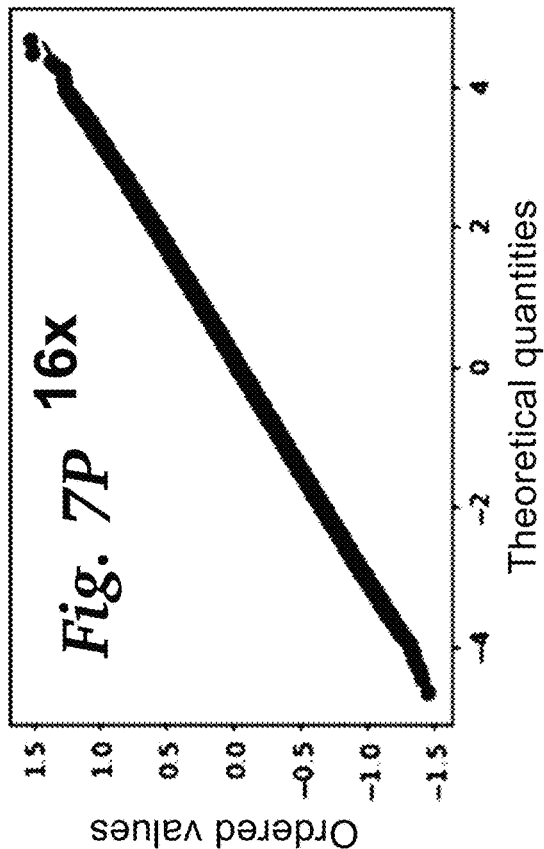
Figure 7O:
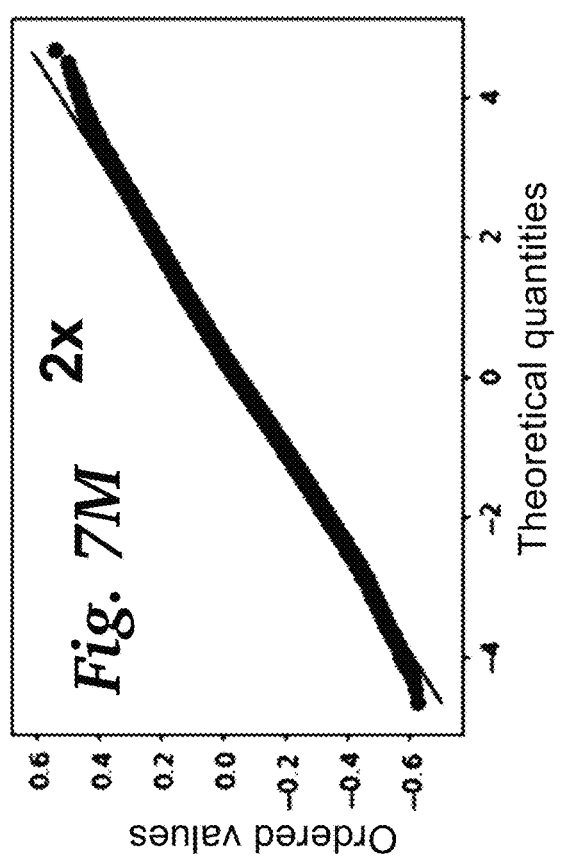
Figure 7P:
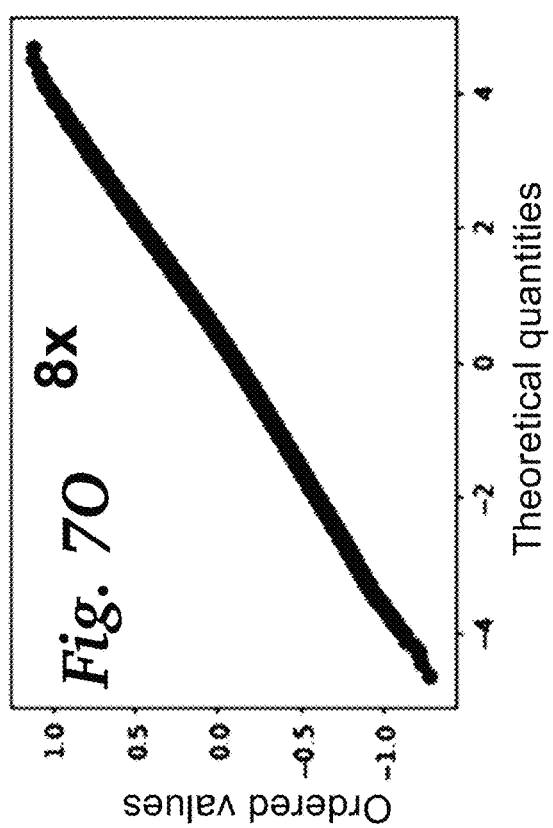

As mentioned before, the key assumption behind SURE is that the residual model is Gaussian with zero mean. However, it is not safe to assume that the undersampling noise in MRI reconstruction inherits this property. For this reason, we introduce density compensation on the input image as a way of enforcing zero-mean residuals for the single coil setting. This approach has the added benefit of making artifacts independent of the underlying image and we find that it significantly increases residual normality (see FIGS. 7A-P).

More specifically, given a 2D sampling mask $\Omega$, we can treat each element of the mask as a Bernouli random variable with a certain probability $D_{i,j}$, where $E[\Omega]=D$ (this is dependent on the sampling approach).

With this formulation, we can define a density compensated zero-filled image as follows: $\tilde{x}_{zf} F^{-1} D^{-1} \Omega F x_0$. We can rewrite this expression using $x_0$ as $$\tilde{x}_{zf} = x_0 + (F^{-1} D^{-1} \Omega F - I) x_0. \tag{13}$$

First, we observe that r has zero mean since $E[D^{-1}\Omega]=I$. In addition, the residual variance obeys $$\sigma = tr(x_0^H (F^{-1} D^{-1} F - I) x_0). \tag{14}$$

Of course, in practice we do not have access to the ground truth image $x_0$, and instead rely on the approximation in (9) for the residual variance. Given these main properties, the density compensation method that this work introduces represents an important step that can allow denoising SURE to be used effectively in medical imaging and other inverse problems. Algorithm 2 summarizes the steps for using density-compensated SURE in practice. Note that for the multi-coil case, density compensation can be extended to adjust for the coil effects using an initial input reconstruction such as SENSE.

Remark 2 [SURE beyond Gaussian residuals]. The primary assumption behind the SURE derivations is that the residuals obey an independent and identically distributed (i.i.d.) Gaussian distribution. Even though the density compensation in (13) enforces this property, one can also leverage the generalized SURE formulation that extends SURE derivations to colored noise distributions from the exponential family, though this is harder to compute in practice [21], [34]. Generalized SURE can be especially useful in the case of uniform sampling, with structured residuals.

Algorithm 2 SURE risk estimate (with density compensation)
Input $y, \Omega, D, n, h, b, \epsilon$
Step 1. Form density-compensated input $\tilde{x}_{zf} F^{-1} D^{-1} \Omega F \Phi^H y$
Step 2. Reconstruct $\hat{x} = h(\tilde{x}_{zf})$
Step 3. Compute the residual variance $\sigma^2 = \|\hat{x} - \tilde{x}_{zf}\|^2 / n$
Step 4. Approximate the DOF: $tr\{J\} \approx b^T (h(\tilde{x}_{zf} + \epsilon b) - h(\tilde{x}_{zf})) \epsilon^{-1}$
Step 5. Obtain SURE risk for $\hat{x}$: $SURE = \sigma^2 tr\{J\}$
return SURE Empirical Evaluations In this section, we assess our model and methods on a dataset of Knee MR images. We first show reconstructions produced with the VAE model, before demonstrating representative results with the Monte Carlo and SURE methods for quantifying uncertainty. Here, we focus on the single coil acquisition model for simplicity, although the techniques can also be extended to the multi-coil model.

Dataset. The Knee dataset utilized in training and testing was obtained from 19 patients with a 3T GE MR750 scanner [35]. A 3D FSE CUBE sequence with proton density weighting including fat saturation was used for acquiring fully sampled images. The following parameters were used in acquisition: FOV=160 mm, TR=1550 for sagittal and 2,000 for axial, TE=25 for sagittal and 35 for axial, slice thickness=0.6 mm for sagittal and 2.5 mm for axial. Each volume consisted of 320 2D axial slices of dimension 320×256, with all slices for a given patient being placed into either the training, validation, or test sets. A 5-fold variable density undersampling mask with radial view ordering (designed to preserve low-frequency structural elements) was used to produce aliased input images $x_{in}$ for the model to reconstruct [36]. Both inputs and outputs of the model are complex valued, with the real and imaginary components considered as two separate channels, which enables simple processing by the network.

A. Adversarial Loss

The effective modeling of high-frequency components is essential for capturing details in medical images. Thus, we train our model with adversarial loss in a GAN setup, which can better capture high-frequency details and has been shown to improve the perceptual quality of recovered images (even though reconstruction error rises) [7], [11]. In particular, we use a multi-layer CNN as the discriminator D along with the VAE generator G. The discriminator learns to distinguish between reconstructions and fully-sampled images, and sends feedback to the generator, which in turn adjusts the VAE's model weights to produce more realistic reconstructions.

The training process for the VAE is identical to the case with no adversarial loss, except an extra loss term is needed to capture the discriminator feedback (with weight $\lambda$ referred to as GAN loss)

$$\min_G E_{x,y}[\|\hat{x} - x_0\|_2^2] + \eta KL(N(\mu_z, \sigma_z) \| N(0,1)) + \lambda E_y[(1 - D(\hat{x}))^2] \tag{15}$$

The discriminator weights are updated during training as $$\min_D E_x[(1 - D(x))^2] + E_y[(D(\hat{x}))^2]. \tag{16}$$

The training process acts as a game, with the generator continuously improving its reconstructions and the discriminator distinguishing them from ground truth. As the GAN loss $\lambda$ increases, the modeling of realistic image components is enhanced but uncertainty rises.

B. Network Architecture

As shown in FIG. 3, the VAE encoder is composed of 4 convolutional layers (128, 256, 512, and 1024 feature maps, respectively) with kernel size 5×5 and stride 2, with each followed by ReLU activations and batch normalization [37]. Latent space mean, $\mu$, and standard deviation, a, correspond to the whole input rather than each channel and are each represented by fully connected layers with 1024 neurons. The VAE decoder has 5 layers and utilizes transpose convolution operations (1024, 512, 256, 128, and 2 feature maps, respectively) with kernel size 5×5 and stride 2 for upsampling [38]. Skip connections are utilized to improve gradient flow through the network [39].

The discriminator function of the GAN (when adversarial loss is used) is an 8-layer CNN. The first seven layers are convolutional (8, 16, 32, 64, 64, 64, and 1 feature maps, respectively) with batch normalization and ReLU activations in all but the last layer. The first five layers use kernel size 3×3, while the following two use kernel size 1×1. The first four layers use a stride of 2, while the next three use a stride of 1. The eighth and final layer averages the output of the seventh layer to form the discriminator output.

The use of multiple recurrent blocks (RB) whereby the model repeats (the output feeds into the input of another VAE with the same model parameters) is also explored [29]. Using multiple RBs does not affect the discriminator network architecture, and the number of RBs can be optimized to maximize model performance as described in [29].

Training was completed over the course of 30,000 iterations, with loss converging over roughly 20,000 iterations. We utilize the Adam optimizer with a mini-batch size of 4, an initial learning rate of $5 \times 10^{-5}$ that was halved every 5000 iterations, and a momentum parameter of 0.9. Models and experiments were developed using TensorFlow on an NVIDIA Titan X Pascal GPU with 12 GB RAM.

C. Individual Reconstructions

Figure 4:
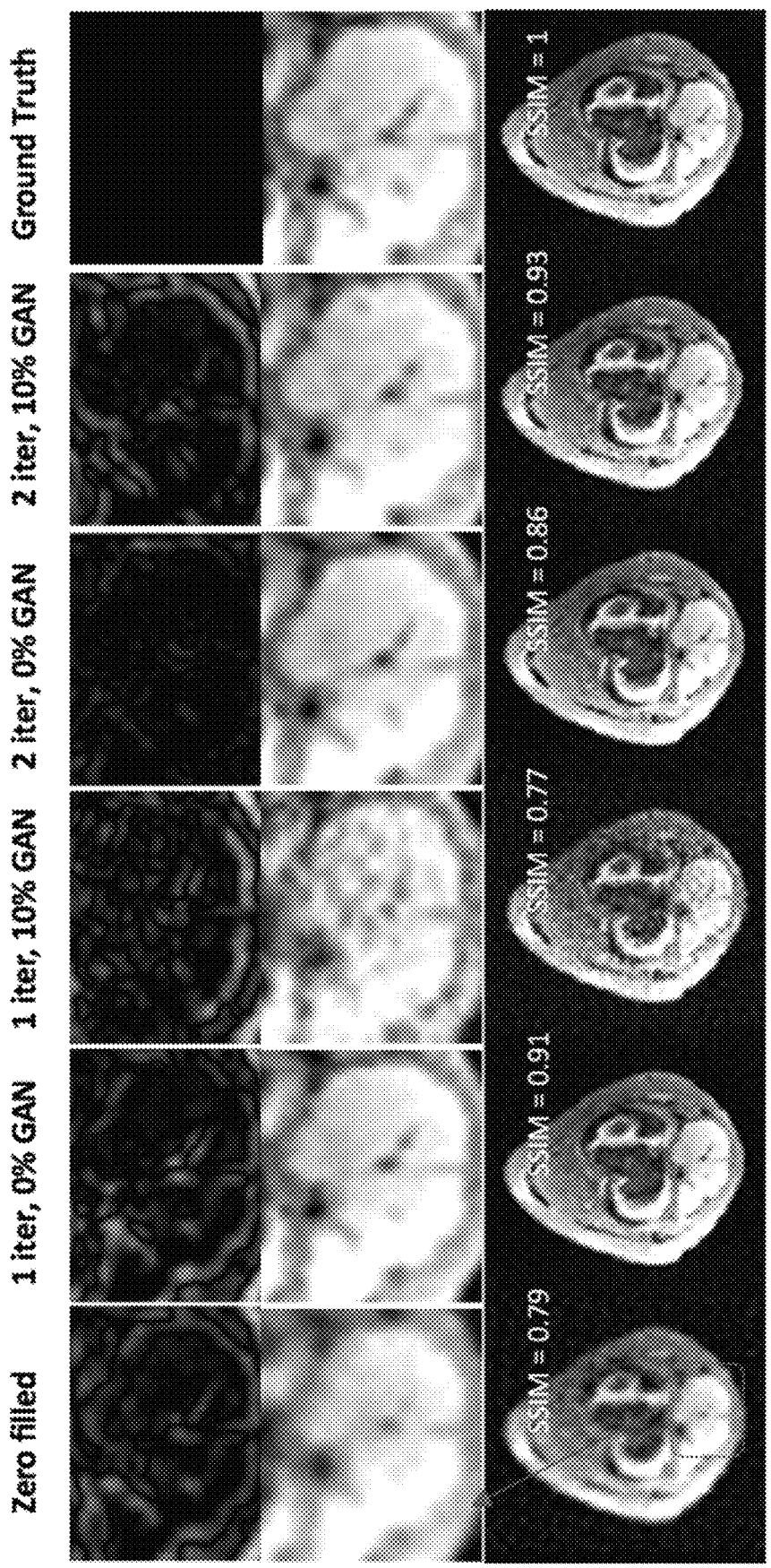
FIG. 4. The aliased input, reconstructions with one recurrent block (RB) and pure MSE loss, one RB and 10 percent GAN loss, two RBs and pure MSE loss, and two RBs and 10 percent GAN loss, and the ground truth for a representative slice (5-fold undersampling with radial view ordering). SSIM between the given image and the ground truth is shown for all cases. The top row shows absolute error for the highlighted ROI. All error images are on the same scale from 0 (black) to 1 (white).

FIG. 4 shows sample model reconstructions (using the mean of the output distribution) for representative test slices with different hyperparameters. As the number of RBs increases from one to two (columns 2 and 3 versus 4 and 5), the resulting outputs improve in quality (corresponding to a roughly 1 dB gain in SNR). Additionally, progressively increasing values of GAN loss (columns 2 and 4 versus 3 and 5) introduce high-frequency artifacts to the image, while leading to sharper outputs. The SSIM results shown in FIG. 4 confirm that using GAN loss can lead to better perceptual quality of the reconstructions, but these benefits are only realized when using additional RBs. Indeed, the highlighted ROI with 1 RB and adversarial loss shows degradation in visual quality from poor recovery, which is detrimental to radiologist diagnoses. As expected, the presence of substantial adversarial loss decreases average reconstruction SNR (and increases MSE) as Table I shows. With limited GAN loss and additional RBs, though, the SNR is close to 20 dB, indicating that the probabilistic model results in effective image recovery, in addition to facilitating uncertainty analysis.

D. Variance, Bias, and Error Maps

Using the Monte Carlo method described earlier in Algorithm 1, 1K outputs corresponding to different reference slices were generated after feeding a test image into the trained model and sampling from the resulting posterior distribution. Note that for this process, only the VAE (generator portion) of the model is relevant to producing outputs, even with adversarial loss used for training.

Figure 5:
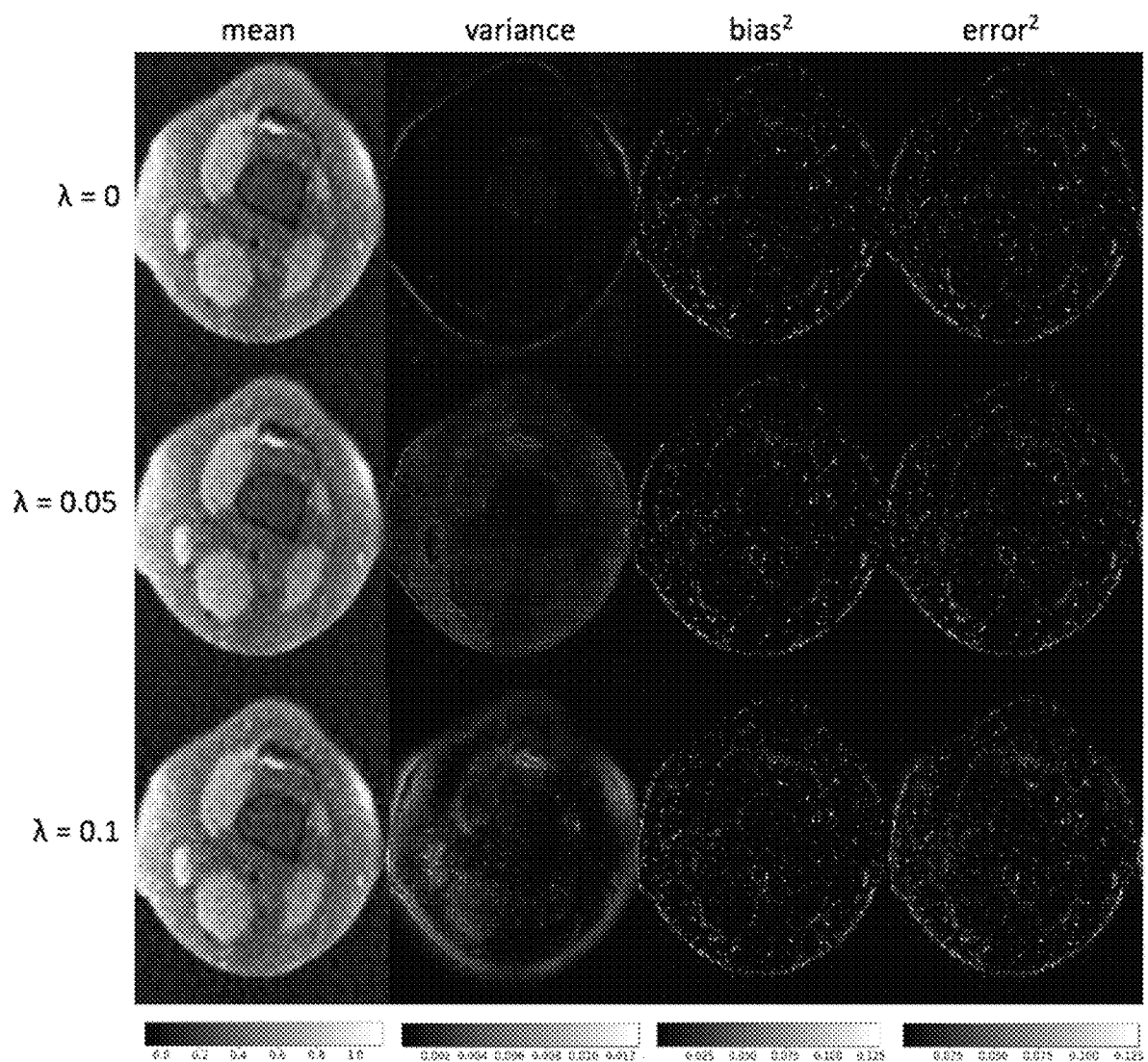
FIG. 5. Mean reconstruction, pixel-wise variance, bias$^2$, and error$^2$ for a given reference slice across all realizations (5-fold undersampling and one recurrent block). Row 1: 0% GAN loss ($\lambda$=0). Row 2: 5% GAN loss ($\lambda$=0.05). Row 3: 10% GAN loss ($\lambda$=0.10).
Figure 6:
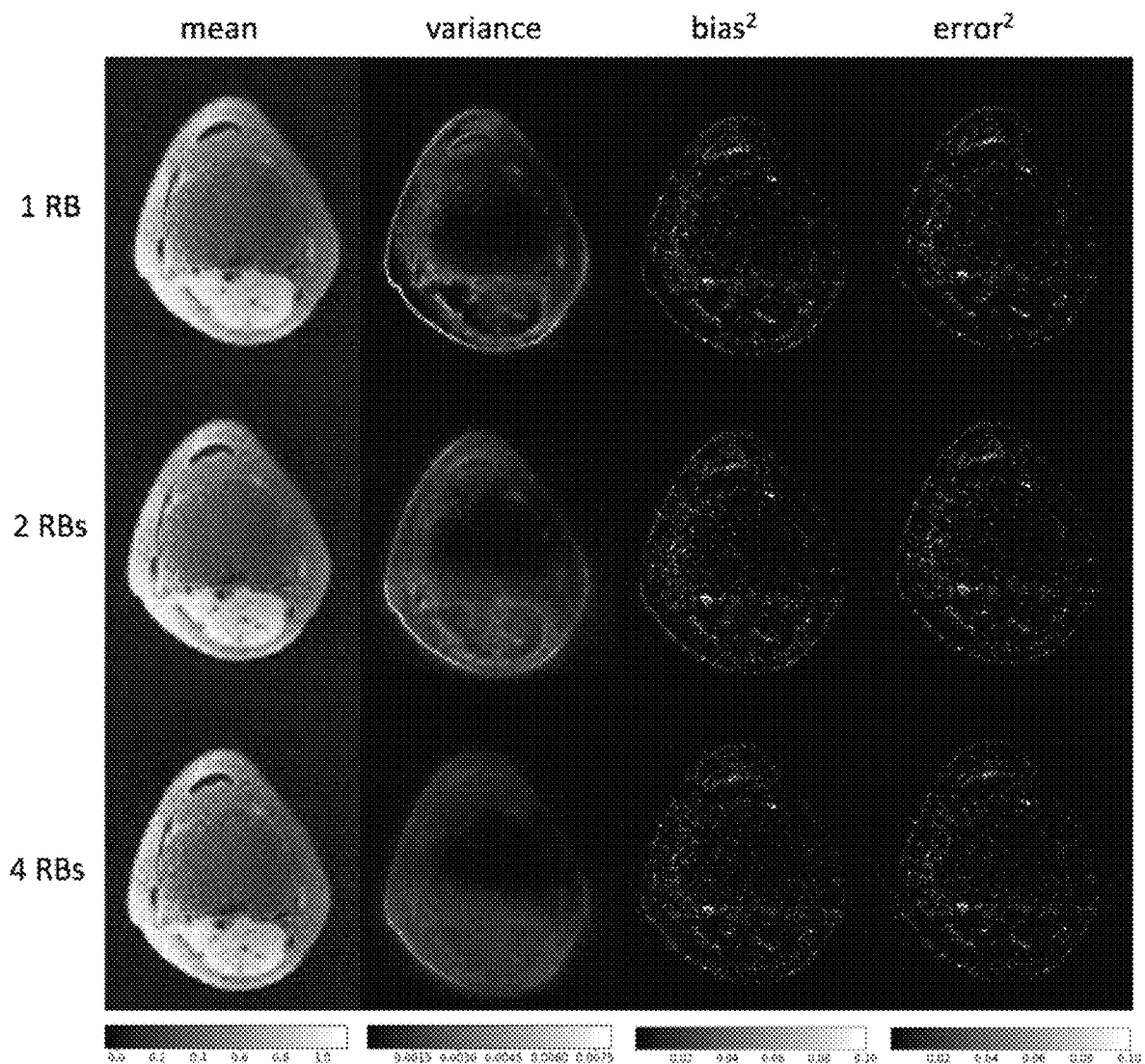
FIG. 6. Mean reconstruction, pixel-wise variance, bias$^2$, and error$^2$ for a given reference slice across all realizations (5-fold undersampling and no adversarial loss). Row 1: one RB. Row 2: two RBs. Row 3: four RBs.

We show the mean of the 1K reconstructed outputs for a representative slice, the pixel-wise variance, squared bias (difference between mean reconstruction and ground truth), and squared error in FIG. 5 and FIG. 6, utilizing the common relation error$^2$=bias$^2$+variance [40]. The mean image shows pixel intensities, while the remaining columns are in squared pixel intensities. The concept of bias and variance is important in the analysis of uncertainty because both the difference from the ground truth and the inherent variability across realizations provide information on the portions of a given image most susceptible to the introduction of realistic artifacts. Note that to compute the bias and error, we need the ground-truth which is provided here solely for validation purposes.

The results indicate that variance, bias, and error increase as the GAN loss weight $\lambda$ increases (FIG. 5) and as the number of RBs decreases (FIG. 6). Furthermore in all cases with GAN loss, the variance extends to structural components of the image, which poses the most danger in terms of diagnosis. Nevertheless, with a reasonably conservative choice of GAN weight, the risk is substantially lower. More RBs can lower variance as well as error, and can be a useful tweak to improve robustness. Note also that in these cases the bias term is more influential than the variance term in contributing to overall error, though the bias cannot be computed in practice since the ground truth is unknown. Although only a few representative examples are shown here, similar trends were observed with all examined reference slices.

TABLE I

AVERAGED RESULTS FOR DIFFERENT QUANTITIES OF RECURRENT BLOCKS AND ADVERSARIAL LOSS WITH 5-FOLD UNDERSAMPLING

| Metrics | 1RB, 0% GAN | 1RB, 10% GAN | 2RB, 0% GAN | 2RB, 10% GAN |
|---|---|---|---|---|
| SURE-MSE $R^2$ | 0.95 | 0.88 | 0.95 | 0.91 |
| MSE | 0.033 | 0.082 | 0.027 | 0.057 |
| RSS | 0.092 | 0.12 | 0.076 | 0.11 |
| DOF | 0.17 | 0.20 | 0.16 | 0.17 |
| SNR (dB) | 18.8 | 17.1 | 19.9 | 17.9 |
| SURE (dB) | 18.0 | 16.2 | 19.2 | 17.3 |

TABLE II

AVERAGED RESULTS FOR DIFFERENT UNDERSAMPLING RATES WITH ONE RECURRENT BLOCK AND NO ADVERSARIAL LOSS

| Metrics | 2-fold | 4-fold | 8-fold | 16-fold |
|---|---|---|---|---|
| SURE-MSE $R^2$ | 0.97 | 0.90 | 0.92 | 0.84 |
| MSE | 0.017 | 0.021 | 0.18 | 0.39 |
| RSS | 0.061 | 0.065 | 0.11 | 0.13 |
| DOF | 0.12 | 0.16 | 0.23 | 0.29 |
| SNR (dB) | 20.7 | 19.1 | 16.8 | 15.5 |
| SURE (dB) | 21.3 | 19.8 | 15.9 | 14.2 |

E. Residual Distribution with Density Compensation

As described earlier, denoising SURE builds on the Gaussian assumption for the residuals $r=x_{zf}-x_0$. To validate this assumption, we produce histograms and Q-Q plots of the residuals at various undersampling rates, by considering the differences for individual pixels across test images. From FIGS. 7A-H one can observe the quantiles closer to the center of the distribution are aligned with those of the normal distribution for all undersampling rates. The residual distribution is not perfectly normal in any of the cases, however, which can limit the effectiveness and accuracy of SURE.

To overcome the lack of normality in the residuals, we apply our density compensation method. For a given undersampling rate, 100 variable-density random sampling masks are generated and then averaged to obtain the sampling density D. The element-wise inverse of this density can then be multiplied with any given mask to produce a density-adjusted mask $D^{-1}\Omega$. This adjusted mask can be used to generate new zero-filled images as input to the network.

As FIGS. 7I-P show, the distribution of residuals (for various undersampling rates) better matches the normal distribution, and the mean of the distribution lies very close to zero. This observation indicates density compensation is a valuable preprocessing step that enables the use of denoising SURE for quantifying uncertainty in MRI reconstruction. Additional experiments have indicated that density compensation can also help produce Gaussian residuals for other sampling trajectories such as uniform, but further work remains to validate and extend this method to all approaches.

F. SURE Results

To evaluate the effectiveness of the density-compensated SURE approach, we produce correlations of SURE versus MSE (which depends on the ground truth and is a standard metric for assessing model error) using the results from our test images. FIGS. 8A, 8B, 8C, 8D show the strong linearity of the correlations under all conditions. The linear relationship is strongest for higher undersampling rates ($R^2$=0.97 for 2-fold while $R^2$=0.84 for 16-fold). Nonetheless, the results show that even with relatively high undersampling, SURE can be used to effectively estimate risk in medical image reconstructions.

In addition, the average reconstruction SURE, RSS, and DOF values for different hyperparameters are shown in Table I and Table II. Increased GAN loss results in decreased SURE values (note the units of dB) and increased RSS and DOF. Meanwhile, more RBs result in higher SURE values and lower RSS and DOF, demonstrating a simple way of improving reconstruction quality while reducing uncertainty. Note that these results align closely with the Monte Carlo analysis from before, thereby reinforcing the effectiveness of the SURE approach in quantifying risk.

Figure 9:
FIG. 9. Sagittal reconstructions (top row) along with corresponding variance maps (5-fold undersampling and one recurrent block with no adversarial loss) and average pixel risk (SURE) values.

Furthermore, the uncertainty analysis of the sample reconstructions in FIG. 9 indicates that there is a relationship between SURE values and variance magnitude. As overall variance decreases from left to right, the SURE values (again, in dB) increase correspondingly.

Figure 10:
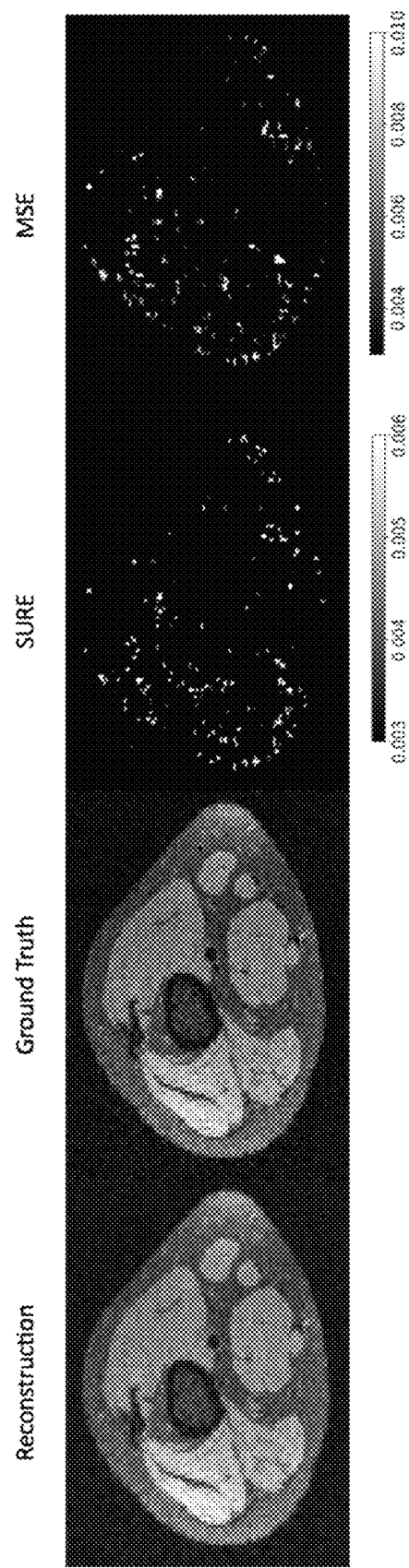
FIG. 10. Pixel-wise SURE and MSE images for a given reference slice with 2-fold undersampling (reconstruction and ground truth are on a scale from 0 to 1). We threshold values below 15% of the max for the SURE and MSE visualizations to make the key regions stand out.

FIG. 10 shows pixel-wise SURE and MSE maps for a given reference slice. The SURE approximation is reasonably effective, with substantial overlap in the areas with highest reconstruction error. It is likely that further work on assessing pixel-wise risk by taking into account the whole input image or developing better residual variance estimators could yield superior results in general. In practice, all of the presented methods can be used in conjunction, with the variance maps and pixel-wise SURE illustrating the localization of uncertainty and global SURE providing a statistically sound overall metric.

CONCLUSIONS

We have disclosed methods to analyze uncertainty in deep-learning based compressive MR image recovery, which can ultimately serve to improve the medical imaging workflow in both better diagnosis and acquisition. To thoroughly explore realistic and data-consistent images, we develop a probabilistic VAE model with low error. A Monte-Carlo approach is used to quantify the pixel variance and obtain uncertainty maps in parallel with reconstruction. Moreover, to fully assess the reconstruction risk (which requires the bias and thus fully sampled data), we leverage Stein's Unbiased Risk Estimator on density-compensated zero-filled images where the residuals obey a zero-mean Gaussian distribution. We validate the utility of these tools with evaluations on a dataset of Knee MR images.

In particular, our observations demonstrate that increased adversarial loss leads to larger uncertainty, indicating a trade-off when using adversarial loss to better retrieve high frequencies. On the other hand, using multiple recurrent blocks (cascaded VAE and data consistency layers), decreases uncertainty, which suggests an effective way of promoting robustness.

While we focus on model uncertainty in this work, there are other sources of uncertainty (pertaining to data and knowledge) that can also be taken into account. Evaluations with different MRI datasets and acquisition strategies may be used to assess the effects of data uncertainty on model reconstructions. Additionally, uncertainty analysis may be useful for pathological cases. Quantifying the likelihood of a diagnosis being altered by hallucinated artifacts, and finding regularization schemes to limit this, will improve the effectiveness of DL methods for MRI reconstruction.

Finally, extending pixel-wise SURE to include more accurate estimators for variance can further improve performance. The corresponding spatial risk maps can then be used alongside the Monte-Carlo results and the global SURE score to improve the medical imaging workflow in key areas such as diagnosis or automated image quality assessment.

[1] A. Radford, L. Metz, and S. Chintala, "Unsupervised representation learning with deep convolutional generative adversarial networks," *arXiv preprint arXiv:* 1511.06434, 2015.

[2] T. M. Quan, T. Nguyen-Duc, and W.-K. Jeong, "Compressed sensing mri reconstruction using a generative adversarial network with a cyclic loss," *IEEE Transactions on Medical Imaging*, vol. 37, no. 6, pp. 1488-1497, 2018.

[3] B. Zhu, J. Z. Liu, S. F. Cauley, B. R. Rosen, and M. S. Rosen, "Image reconstruction by domain-transform manifold learning," *Nature*, vol. 555, no. 7697, p. 487, 2018.

[4] D. Lee, J. Yoo, and J. C. Ye, "Deep residual learning for compressed sensing MRI," in *Biomedical Imaging (ISBI 2017), 2017 IEEE 14th International Symposium on*. IEEE, 2017, pp. 15-18.

[5] A. Bora, A. Jalal, E. Price, and A. G. Dimakis, "Compressed sensing using generative models," *arXiv preprint arXiv:1703.03208*, 2017.

[6] A. Mousavi, A. B. Patel, and R. G. Baraniuk, "A deep learning approach to structured signal recovery," in *Communication, Control, and Computing (Allerton), 2015 53rd Annual Allerton Conference on*. IEEE, 2015, pp. 1336-1343.

[7] M. Mardani, E. Gong, J. Y. Cheng, S. S. Vasanawala, G. Zaharchuk, L. Xing, and J. M. Pauly, "Deep generative adversarial neural networks for compressive sensing (GANCS) MRI," *IEEE Transactions on Medical Imaging*, 2018.

[8] A. Kendall and Y. Gal, "What uncertainties do we need in bayesian deep learning for computer vision?" in *Advances in neural information processing systems*, 2017, pp. 5574-5584.

[9] F. E. Harrell, K. L. Lee, and D. B. Mark, "Multivariable prognostic models: issues in developing models, evaluating assumptions and adequacy, and measuring and reducing errors," *Statistics in medicine*, vol. 15, no. 4, pp. 361-387, 1996.

[10] H. Emami, M. Dong, S. P. Nejad-Davarani, and C. K. Glide-Hurst, "Generating synthetic CTs from magnetic resonance images using generative adversarial networks," *Medical physics*, vol. 45, no. 8, pp. 3627-3636, 2018.

[11] A. B. L. Larsen, S. K. Sønderby, H. Larochelle, and O. Winther, "Autoencoding beyond pixels using a learned similarity metric," in *International Conference on Machine Learning*, 2016, pp. 1558-1566.

[12] L. Cai, H. Gao, and S. Ji, "Multi-stage variational auto-encoders for coarse-to-fine image generation," in *Proceedings of the 2019 SIAM International Conference on Data Mining*. SIAM, 2019, pp. 630-638.

[13] K. Mosegaard and A. Tarantola, "Monte carlo sampling of solutions to inverse problems," *Journal of Geophysical Research: Solid Earth*, vol. 100, no. B7, pp. 12431-12447, 1995.

[14] J. Adler, A. Ringh, O. Öktem, and J. Karlsson, "Learning to solve inverse problems using wasserstein loss," arXiv preprint arXiv:1710.10898, 2017.

[15] R. Tanno, D. Worrall, E. Kaden, A. Ghosh, F. Grussu, A. Bizzi, S. N. Sotiropoulos, A. Criminisi, and D. C. Alexander, "Uncertainty quantification in deep learning for safer neuroimage enhancement," arXiv preprint arXiv:1907.13418, 2019.

[16] L. Ardizzone, J. Kruse, S. Wirkert, D. Rahner, E. W. Pellegrini, R. S. Klessen, L. Maier-Hein, C. Rother, and U. Köthe, "Analyzing inverse problems with invertible neural networks," arXiv preprint arXiv:1808.04730, 2018.

[17] A. C. Gilbert, Y. Zhang, K. Lee, Y. Zhang, and H. Lee, "Towards understanding the invertibility of convolutional neural networks," arXiv preprint arXiv:1705.08664, 2017.

[18] T. Küstner, A. Liebgott, L. Mauch, P. Martirosian, F. Bamberg, K. Nikolaou, B. Yang, F. Schick, and S. Gatidis, "Automated reference-free detection of motion artifacts in magnetic resonance images," *Magnetic Resonance Materials in Physics, Biology and Medicine*, vol. 31, no. 2, pp. 243-256, 2018.

[19] M. Tygert, R. Ward, and J. Zbontar, "Compressed sensing with a jackknife and a bootstrap," arXiv preprint arXiv:1809.06959, 2018.

[20] F. Luisier, T. Blu, and M. Unser, "A new sure approach to image denoising: Interscale orthonormal wavelet thresholding," *IEEE Transactions on image processing*, vol. 16, no. 3, pp. 593-606, 2007.

[21] C. Deledalle, S. Vaiter, G. Peyré, J. Fadili, and C. Dossal, "Unbiased risk estimation for sparse analysis regularization," in *2012 19th IEEE International Conference on Image Processing*. IEEE, 2012, pp. 3053-3056.

[22] K. Hynynen, A. Darkazanli, E. Unger, and J. Schenck, "MRI-guided noninvasive ultrasound surgery," *Medical Physics*, vol. 20, no. 1, pp. 107-115, 1993.

[23] S. S. Vasanawala and M. Lustig, "Advances in pediatric body MRI," *Pediatric radiology*, vol. 41, no. 2, p. 549, 2011.

[24] L. Xu, J. S. Ren, C. Liu, and J. Jia, "Deep convolutional neural networks for image deconvolution," in *Advances in Neural Information Processing Systems*, 2014, pp. 1790-1798.

[25] G. Yang, S. Yu, H. Dong, G. Slabaugh, P. L. Dragotti, X. Ye, F. Liu, S. Arridge, J. Keegan, Y. Guo et al., "DAGAN: Deep de-aliasing generative adversarial networks for fast compressed sensing MRI reconstruction," *IEEE Transactions on Medical Imaging*, vol. 37, no. 6, pp. 1310-1321, 2018.

[26] K. P. Pruessmann, M. Weiger, M. B. Scheidegger, and P. Boesiger, "SENSE: sensitivity encoding for fast MRI," *Magnetic Resonance in Medicine: An Official Journal of the International Society for Magnetic Resonance in Medicine*, vol. 42, no. 5, pp. 952-962, 1999.

[27] A. Dosovitskiy and T. Brox, "Generating images with perceptual similarity metrics based on deep networks," in *Advances in Neural Information Processing Systems*, 2016, pp. 658-666.

28] D. P. Kingma and M. Welling, "Auto-encoding variational Bayes," arXiv preprint arXiv:1312.6114, 2013.

[29] M. Mardani, Q. Sun, S. Vasanawala, V. Papyan, H. Monajemi, J. Pauly, and D. Donoho, "Neural proximal gradient descent for compressive imaging," in *Advances in Neural Information Processing Systems*, 2018, pp. 9573-9583.

[30] R. J. Tibshirani and S. Rosset, "Excess optimism: How biased is the apparent error of an estimator tuned by SURE?" *Journal of the American Statistical Association*, pp. 1-16, 2018.

[31] D. Jakubovitz and R. Giryes, "Improving dnn robustness to adversarial attacks using jacobian regularization," in *Proceedings of the European Conference on Computer Vision (ECCV)*, 2018, pp. 514-529.

[32] S. Ramani, T. Blu, and M. Unser, "Monte-carlo SURE: A black-box optimization of regularization parameters for general denoising algorithms," *IEEE Transactions on image processing*, vol. 17, no. 9, pp. 1540-1554, 2008.

[33] C. A. Metzler, A. Mousavi, R. Heckel, and R. G. Baraniuk, "Unsupervised learning with Stein's unbiased risk estimator," arXiv preprint arXiv:1805.10531, 2018.

[34] Y. C. Eldar, "Generalized SURE for exponential families: Applications to regularization," *IEEE Transactions on Signal Processing*, vol. 57, no. 2, pp. 471-481, 2009.

[35] http://mridata.org/.

[36] J. Y. Cheng, T. Zhang, M. T. Alley, M. Lustig, S. S. Vasanawala, and J. M. Pauly, "Variable-density radial view-ordering and sampling for time-optimized 3D cartesian imaging," in *Proceedings of the ISMRM Workshop on Data Sampling and Image Reconstruction*, 2013.

[37] A. van den Oord, O. Vinyals et al., "Neural discrete representation learning," in *Advances in Neural Information Processing Systems*, 2017, pp. 6306-6315.

[38] S. Jégou, M. Drozdzal, D. Vazquez, A. Romero, and Y. Bengio, "The one hundred layers tiramisu: Fully convolutional densenets for semantic segmentation," in *Computer Vision and Pattern Recognition Workshops (CVPRW), 2017 IEEE Conference on*. IEEE, 2017, pp. 1175-1183.

[39] A. B. Dieng, Y. Kim, A. M. Rush, and D. M. Blei, "Avoiding latent variable collapse with generative skip models," arXiv preprint arXiv:1807.04863, 2018.

[40] R. Tibshirani, *Bias, variance and prediction error for classification rules*. Citeseer, 1996.

The invention claimed is:

1. A method for generating pixel risk maps for diagnostic image reconstruction comprising:
  feeding into a trained encoder a short-scan image acquired from a medical imaging scan to generate latent code statistics including the mean $\mu_y$ and variance $\alpha_y$;
  selecting random samples z based on the latent code statistics, where the random samples z are sampled from a normal distribution as $z \sim N(\mu_y, \sigma_y^2)$ where N represents a normal distribution function;
  feeding the random samples into a trained decoder to generate a pool of reconstructed images;
  calculating, for each pixel across the pool of reconstructed images, pixel-wise mean and variance statistics across the pool of reconstructed images;
  computing an end-to-end Jacobian of a reconstruction network that is fed with a density-compensated short-scan image, and estimating a risk of each pixel across the pool of reconstructed images, based on a Stein Unbiased Risk Estimator (SURE).

2. The method of claim 1 further comprising calculating quantitative scores for risk of each pixel of the pool of reconstructed images.

* * * * *